United States Patent [19]

Mineo et al.

[11] Patent Number: 5,874,643
[45] Date of Patent: Feb. 23, 1999

[54] HYPOPHOSPHOROUS ACID TO STABILIZE FATTY ALCOHOLS

[75] Inventors: Garrett Mineo, Marrero; Michael Denoux, Metairie, both of La.

[73] Assignee: Witco Corporation, Greenwich, Conn.

[21] Appl. No.: 566,064

[22] Filed: Dec. 1, 1995

[51] Int. Cl.⁶ .............................. C07C 27/26; C07C 29/94
[52] U.S. Cl. .......................... 568/701; 568/913; 554/167; 554/4; 554/190
[58] Field of Search .............................. 584/167, 4, 190; 568/913, 920, 701

[56] References Cited

PUBLICATIONS

Chem. abstr., Il'na et al, 91:2202, 1979.
Chem. abstr., Kumar et al., 106:196166, 1986.

*Primary Examiner*—Gary Geist
*Assistant Examiner*—Deborah D Carr
*Attorney, Agent, or Firm*—Edward K. Welch, Esq.; Timothy X. Witkowski, Esq.; Andrew S. Reiskind, Esq.

[57] ABSTRACT

Fatty alcohol containing admixed therewith a small amount on the order of up to 1.0 wt. % of hypophosphorous acid, exhibits markedly reduced oxidation and oxidation-related deterioration such as discoloration and other side effects. This discovery is particularly useful when the fatty alcohol is subjected to reactions such as esterification under conditions which could cause or accelerate undesired oxidation.

26 Claims, No Drawings

HYPOPHOSPHOROUS ACID TO STABILIZE FATTY ALCOHOLS

BACKGROUND OF THE INVENTION

The present invention relates to the stabilization of fatty organic compounds, and particularly fatty alcohols and derivatives thereof.

The present invention also relates to the synthesis, particularly on an industrial scale, of fatty alcohol derivatives wherein the reactants and their derivatives may be subject to undesired side reaction such as oxidation. Unwanted oxidation, whether with atmospheric oxygen or with other oxidizing reactants, is a particularly well-known side reaction which those who work in this field would like to avoid because it leads to undesired side effects such as unpleasant odors and loss of the desired color in the product.

It has long been known that fatty organic compounds, particularly those derived from natural sources, can be subject to undesired oxidation, particularly when the compound in question is in the liquid state; and particularly in the presence of acids such as sulfuric or sulfuric acids. This phenomenon is well known as to fatty alcohols, such as stearyl alcohol. For this reason, such products are frequently stored and shipped in the solid state, generally as particles or flakes. However, providing such materials in the solid state frequently involves additional steps of subdividing the product into a manageable form such as flakes, pellets, or otherwise, so as to facilitate operations such as handling, pouring, measuring, and packaging. The steps necessitated in putting such products into particle form necessarily introduce additional equipment and handling requirements which one would desire to eliminate if possible. Indeed, the additional steps necessary to appropriately subdivide the solid materials can cause undesired losses of material and changes in purity, and also require periodic cleaning and maintenance of the equipment used.

Thus, it would be desirable to be able to provide products such as fatty alcohols in liquid form, if only a means were available whereby oxidation of such products could be inhibited or eliminated. The savings in energy and equipment usage as well as in packaging materials required for handling of the particulate solids, would be significant. However, to date there remains an unfilled need for a means for stabilizing fatty compounds such as fatty alcohols against undesired oxidation and the resultant side effects such as color degradation, in a manner which is economical and readily practiced and yet which does not interfere with subsequent reactions or other uses of the fatty material in question.

BRIEF SUMMARY OF THE INVENTION

The present invention solves these needs and provides additional advantages as described herein.

One aspect of the present invention thus comprises a liquid product comprising a fatty alcohol containing 12 to 24 carbon atoms and an effective amount, such as up to about 1.0 wt. %, of hypophosphorous acid to inhibit undesired oxidation of the fatty alcohol in situ or in subsequent reaction thereof.

Another aspect of the present invention is a method of inhibiting oxidation of fatty alcohol containing 12 to 24 carbon atoms, comprising adding thereto hypophosphorous acid in an amount effective to inhibit oxidation of said fatty alcohol.

Other aspects of the present invention relate to the use of hypophosphorous acid to inhibit undesired oxidation in the course of a reaction of fatty alcohol, which reaction is carried out under conditions which might ordinarily give rise to oxidation of the fatty alcohol or the reaction product thereof. Thus, for instance, the present invention also comprises a process for esterifying a fatty alcohol in the liquid state, wherein the alcohol and the product of its esterification undergo little or no oxidation. The process comprises esterifying said fatty alcohol in the liquid state in mixture with hypophosphorous acid, wherein the hypophosphorous acid is present in said mixture in a small amount effective to inhibit oxidation of the alcohol and its ester.

DETAILED DESCRIPTION OF THE INVENTION

It has been discovered that fatty alcohols containing admixed therewith a small amount of hypophosphorous acid exhibit, surprisingly, a diminished tendency to undergo oxidation and exhibit a diminished tendency to exhibit oxidation-related side effects upon the reaction of such fatty compounds, particularly including esterification reactions. By "fatty alcohols" are meant herein monohydric and polyhydric fatty alcohols, particularly those containing 12 to 24 carbon atoms exhibiting straight-chain or branched-chain structure, which are saturated or which contain one or more carbon-carbon double bonds.

The preferred fatty alcohol which is a subject of this invention is stearyl alcohol.

The "oxidation-related" side effects to which stearyl alcohol and other such substances can be subject, include undesired color changes such as a loss of transparency, or a change in color from for instance a white or near-white color to an off-white color which is typically light tan or darker.

The freedom from such oxidation-related side effects is particularly pronounced when a fatty alcohol containing mixed therewith hypophosphorous acid as described herein is subjected to reaction, and particularly to esterification reactions.

In particular, reactions to which fatty alcohols are subjected in the industrial arena, and which are vulnerable to oxidation-related deterioration in the absence of the stabilization provided by the present invention, include esterification with carboxylic acids (containing one or more carboxylic group) including lower alkanoic acids containing e.g. 1 to 6 carbon atoms, as well as esterification with medium length or long-chain fatty acids containing from 6 to 24 or more carbon atoms and one or more carboxylic acid functionality. Other reactions to which this invention is applicable include esterification with sulfur-containing reactants such as thiocarboxylic or thiodicarboxylic acids such as thiodipropionic acid.

Esters are made by the customary procedure, e.g. reacting the fatty alcohol (in admixture with hypophosphorous acid) with the desired acid reactant, under acidic conditions. The esters made by the foregoing esterification reactions in the presence of hypophosphorous acid are useful as lubricants, emollients, mold release agents, and in other applications familiar to the industrial chemist.

Other preferred fatty alcohols to which the present invention is applicable include fatty alcohols such as oleic, linolenic, linolenic, lauric, caproic, myristic and palmitic alcohols, as well as mixtures of any of the foregoing fatty alcohols.

The amount of hypophosphorous acid which should be present in mixture with the fatty alcohol should be an amount sufficient to inhibit oxidation of the fatty alcohol when the fatty alcohol is in the liquid state and exposed to the ambient atmosphere. Those of ordinary skill in this art will readily recognize that the appropriate amount of hypophosphorous acid which provides the desired inhibition of oxidation can readily be ascertained, by a simple comparison of properties (such as, particularly, onset of color or discoloration) as between a sample containing a given amount of hypophosphorous acid and the equivalent sample, subject to the same treatment, but not containing any hypophosphorous acid.

In general, however, effective amounts of hypophosphorous acid will generally be up to about 1.0 wt. % or even up to about 0.1 to 0.5 wt. % based on the amount of the fatty alcohol or alcohols present. Higher amounts will generally be effective, but it can be expected that at sufficiently higher amounts of hypophosphorous acid no additional amount of oxidation inhibition would be realized. Preferably, the amount of hypophosphorous acid which is effective to inhibit oxidation and its related side effects is generally about 0.02% to about 0.075%, and more preferably about 0.05%, expressed as percent by weight of the fatty alcohol or alcohols present.

The hypophosphorous acid is preferably added to the fatty alcohol as soon as it is produced or recovered, or as soon as practicable thereafter. If the fatty alcohol is being stored under conditions limiting its contact with oxygen, the hypophosphorous acid is preferably added before, or as soon as practicable after, exposure to oxygen (even ambient atmospheric oxygen).

It has been found that carrying out reactions, e.g. esterifications, with fatty alcohol to which hypophosphorous acid has previously been added, produces products which are significantly and unexpectedly freer of oxidative degradation than is found when hypophosphorous acid is first added to the fatty alcohol at the time of reaction. This behavior, which is demonstrated in Example 3, is particularly unexpected since one would expect the same given amount of hypophosphorous acid, subjected to the same reaction conditions, to have the same effect whether the hypophosphorous acid is added when the reaction is carried out or is already present. Instead the applicants have found that when the hypophosphorous acid is already present, its beneficial effects are substantially more pronounced.

The hypophosphorous acid should have been present in the fatty alcohol long enough to be equilibrated with the fatty alcohol, i.e. present preferably for at least 1 hour, and more preferably for at least 24 hours.

The invention will be illustrated in the following examples, which are provided for purposes of illustration and which should not be interpreted as exhibiting an intention to limit the scope of the invention described herein.

EXAMPLE 1

Samples (50 grams each) of commercial stearyl alcohol derived from natural sources were placed in each of two 4-ounce jars, and 0.05 g of a 50 wt. % aqueous solution of hypophosphorous acid ("HPA") was added to one of the jars. Both jars were then placed, uncapped, in a 250° F. oven. The heating simulates the conditions to which the stearyl alcohol would be subjected in use as a reactant, and also accelerates the onset of any oxidation. The color (as the "APHA color") was determined after 36, 85 and 146 days in the oven, using "method 120" on a HACH 2000 spectrophotometer. Initially the color was determined in a 10% solution in toluene (approximately 2.6 grams of sample per dilution). When the color exceeded the 500 APHA range of the color determination method, samples were further diluted, as necessary, and the results mathematically converted to correspond to those of a 10 wt. % solution. The results of the color determinations are set forth in Table 1:

TABLE 1

| | APHA Color of 10% Toluene Solution | |
|---|---|---|
| Time (days) | No HPA added | 0.05% HPA added |
| 0 | 0 | 0 |
| 36 | 5 | 3 |
| 85 | 28 | 37 |
| 146 | 8200 | 1040 |

Higher APHA color numbers are associated with the observance of more color and a greater loss of transparency in the sample, which in turn is associated with the sample having undergone a higher degree of oxidation. Thus, the data in Table 1 show that addition of HPA to the sample significantly inhibited the oxidation undergone by the tested sample. The pronounced difference at 146 days indicates a considerable improvement in long-term shelf-life of the fatty alcohol.

EXAMPLE 2

The procedure of Example 1 was repeated except that 0.5 grams of para-toluenesulfonic acid was added to each sample to hasten any color development. The samples were analyzed for color, using the procedure described in Example 1, every 6 hours after they were placed in the oven. The results are set forth in Table 2:

TABLE 2

| | APHA Color of 10% Toluene Solution | |
|---|---|---|
| Time (hrs.) | No HPA Added | 0.05% HPA Added |
| 0 | 0 | 0 |
| 6 | 8 | 6 |
| 12 | 67 | 63 |
| 18 | 123 | 114 |
| 24 | 220 | 165 |
| 30 | 287 | 204 |
| 36 | 356 | 240 |
| 42 | 465 | 348 |
| 48 | 564 | 404 |
| 54 | 1112 | 760 |
| 60 | 1620 | 964 |
| 66 | 2550 | 1200 |
| 72 | 3640 | 2000 |

These results, like the results shown in Table 1, indicate that addition of HPA in accordance with the present invention significantly inhibited oxidation of the fatty alcohol.

EXAMPLE 3

To each of two 16-ounce jars was added a 200 gram sample of a commercial stearyl alcohol derived from natural sources. To one of the jars was added 0.2 g of a 50 wt. % aqueous solution of HPA (providing a content of 0.05 wt. % HPA). The contents of the jars were each mixed and then the jars were placed, loosely capped, in a 200° F. oven. After specific lengths of time in the oven, samples from each jar were removed and subjected to a test in which the stearyl alcohol was reacted with recrystallized thiodipropionic acid ("TDPA") to form distearyl thiodipropionate ("DSTDP"), and the DSTDP was tested for coloration by the technique described in Example 1 except that solutions tested were 50% in toluene. To each sample that had been taken from a jar to which HPA had not previously been added, 0.05 wt. % HPA was added at the time of reaction with the thiodipropionic acid. Table 3 sets forth the color test results:

TABLE 3

| | APHA Color of 50% Toluene Solution | | |
|---|---|---|---|
| Time (days) | No HPA | 0.05% HPA Added Before Placement In Oven | 0.05% HPA Added Only at Rxn. w/TDPA |
| 30 | 40 | 0 | 2 |
| 90 | 4800 | 14 | 2530 |

These results, like the results in Tables 1 and 2, demonstrate that addition of HPA to the fatty alcohol significantly inhibits oxidation and discoloration of the alcohol and of its reaction product. In addition, these results surprisingly show that carrying out the reaction with fatty alcohol to which the hypophosphorous acid has previously been added provides product that is substantially less prone to oxidative degradation.

What is claimed is:

1. A process for inhibiting oxidation of a fatty alcohol containing 12 to 24 carbon atoms, comprising adding to said fatty alcohol an amount of hypophosphorous acid effective to inhibit said oxidation.

2. A process according to claim 1 wherein said fatty alcohol is stearyl alcohol.

3. A process according to claim 1 wherein the amount of said hypophosphorous acid is up to 1.0 wt. % of said fatty alcohol.

4. A process according to claim 3 wherein said fatty alcohol is stearyl alcohol.

5. A process according to claim 1 wherein the amount of said hypophosphorous acid is up to 0.5 wt. % of said fatty alcohol.

6. A process according to claim 5 wherein said fatty alcohol is stearyl alcohol.

7. A composition of matter comprising fatty alcohol containing 12 to 24 carbon atoms and an amount of hypophosphorous acid effective to inhibit oxidation of said fatty alcohol.

8. A composition of matter according to claim 7 wherein said fatty alcohol is stearyl alcohol.

9. A composition of matter according to claim 7 wherein the amount of said hypophosphorous acid is up to 1.0 wt. % of said fatty alcohol.

10. A composition of matter according to claim 9 wherein said fatty alcohol is stearyl alcohol.

11. A composition of matter according to claim 7 wherein the amount of said hypophosphorous acid is up to 0.5 wt. % of said fatty alcohol.

12. A composition of matter according to claim 11 wherein said fatty acid is stearyl alcohol.

13. A process for producing an ester of a fatty alcohol containing 12 to 24 carbon atoms which ester exhibits reduced vulnerability to oxidation; comprising forming a mixture of said fatty alcohol and hypophosphorous acid which is present in said mixture in an amount effective to inhibit oxidation of said alcohol, and thereafter esterifying said fatty alcohol while it is mixed with said hypophosphorous acid.

14. A process according to claim 13 wherein said alcohol is stearyl alcohol.

15. A process according to claim 13 wherein the amount of said hypophosphorous acid is up to about 1.0 wt. % of said fatty alcohol.

16. A process according to claim 15 wherein said alcohol is stearyl alcohol.

17. A process according to claim 13 wherein the amount of said hypophosphorous acid is up to about 0.5 wt. % of said fatty alcohol.

18. A process according to claim 17 wherein said alcohol is stearyl alcohol.

19. A process according to claim 13 wherein said fatty alcohol is esterified with thiodipropionic acid.

20. A process according to claim 19 wherein said fatty alcohol is stearyl alcohol.

21. A process according to claim 19 wherein the amount of said hypophosphorous acid is up to 1.0 wt. % of said fatty alcohol.

22. A process according to claim 21 wherein said fatty alcohol is stearyl alcohol.

23. A process according to claim 19 wherein the amount of said hypophosphorous acid is up to 0.5 wt. % of said fatty alcohol.

24. A process according to claim 23 wherein said fatty alcohol is stearyl alcohol.

25. A process according to claim 13 wherein said mixture of fatty alcohol and hypophosphorous acid is formed at least 1 hour before said fatty alcohol is esterified.

26. A process according to claim 13 wherein said mixture of fatty alcohol and hypophosphorous acid is formed at least 24 hours before said fatty alcohol is esterified.

* * * * *